United States Patent [19]

Dossin

[11] 4,368,729

[45] Jan. 18, 1983

[54] ASEPTIC SYSTEM FOR TOTAL PARENTERAL NUTRITION AND THE LIKE

[75] Inventor: Luc M. Dossin, Braine l'Alleud, Belgium

[73] Assignee: Baxter Travenol Laboratories, Inc., Deerfield, Ill.

[21] Appl. No.: 196,966

[22] Filed: Oct. 14, 1980

[51] Int. Cl.³ .............................................. A61M 5/00

[52] U.S. Cl. .............................. 128/214 D; 128/214.2

[58] Field of Search ............ 128/214 R, 214 D, 214.2, 128/247; 222/80, 81, 83; 141/1, 98

[56] References Cited

U.S. PATENT DOCUMENTS

| | | | |
|---|---|---|---|
| Re. 29,656 | 6/1978 | Chittenden et al. | 128/272.3 |
| 2,849,156 | 8/1958 | Mansted | 222/83 |
| 2,855,131 | 10/1958 | Gewecke et al. | 222/545 |
| 3,127,892 | 4/1964 | Bellamy | 128/214.2 |
| 3,416,528 | 12/1968 | Kahn | 128/214.2 |
| 3,648,693 | 3/1972 | Koremura | 128/214 D |
| 3,685,795 | 8/1972 | Caster | 251/342 |
| 3,902,489 | 9/1975 | Carter | 128/214 R |
| 4,056,116 | 11/1977 | Carter et al. | 128/214.2 |
| 4,080,965 | 3/1978 | Phillips | 128/214.2 |
| 4,157,723 | 6/1979 | Granzow et al. | 141/1 |

FOREIGN PATENT DOCUMENTS

| | | |
|---|---|---|
| 1091292 | 4/1961 | Fed. Rep. of Germany . |
| 6607165 | 11/1966 | Netherlands . |
| 7005300 | 10/1971 | Netherlands . |
| 148502 | 7/1976 | Netherlands . |

*Primary Examiner*—Richard J. Apley
*Assistant Examiner*—T. J. Wallen
*Attorney, Agent, or Firm*—John P. Kirby, Jr.; Garrettson Ellis; Bradford R. L. Price

[57] ABSTRACT

An improved flexible, collapsible container (10) for holding a sterile solution such as protein hydrolysate or amino acid solutions is disclosed, it being intended for sterile connection with another flexible, collapsible container (38) of carbohydrate solutions or the like. The two containers carry connector members (24, 34) of a specific design. A flexible tubular boot member (18) is provided to the container of this invention, which carries the connector and a tubular cannula (20) defining an inwardly-pointed spike adapted to penetrate puncturable diaphragm means (17) for opening the contents in sterile manner. The boot member is of a particular shape as disclosed to permit inward deflection of its end without forcing the sides to expand substantially outwardly.

11 Claims, 4 Drawing Figures

FIG. 1
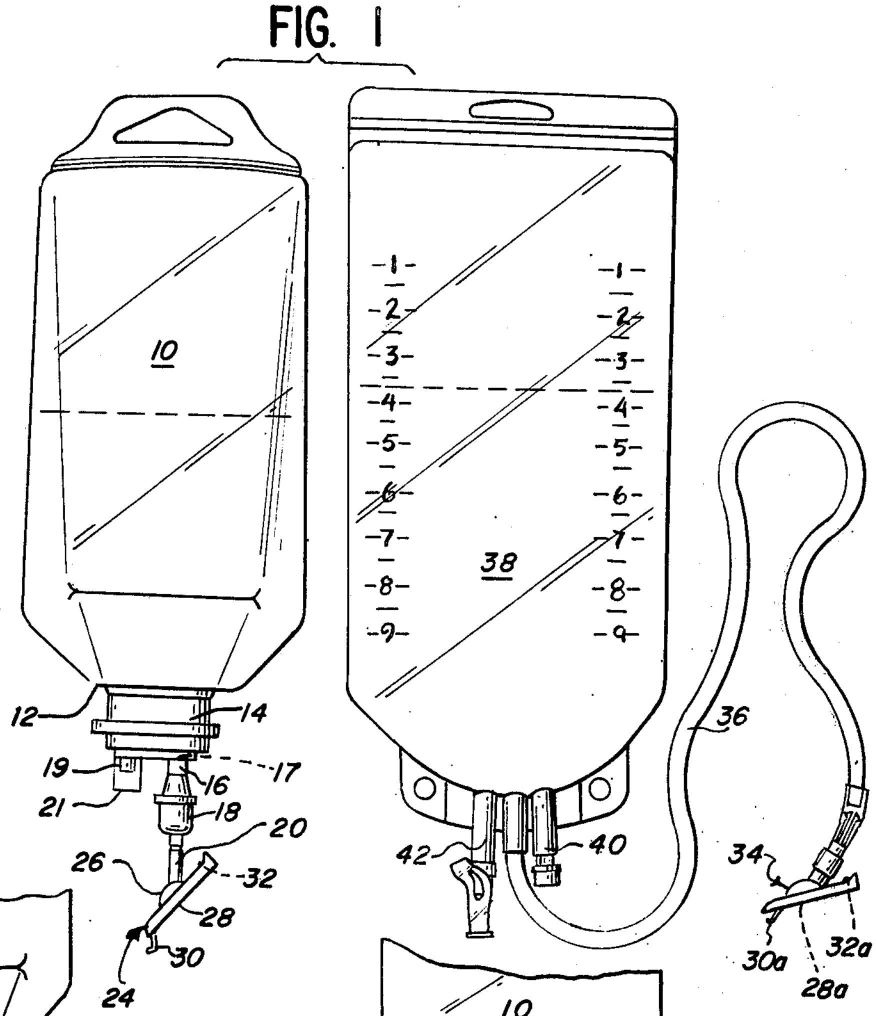
FIG. 2
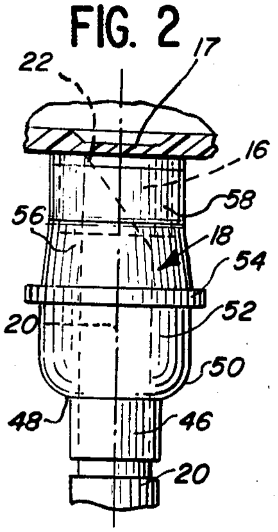
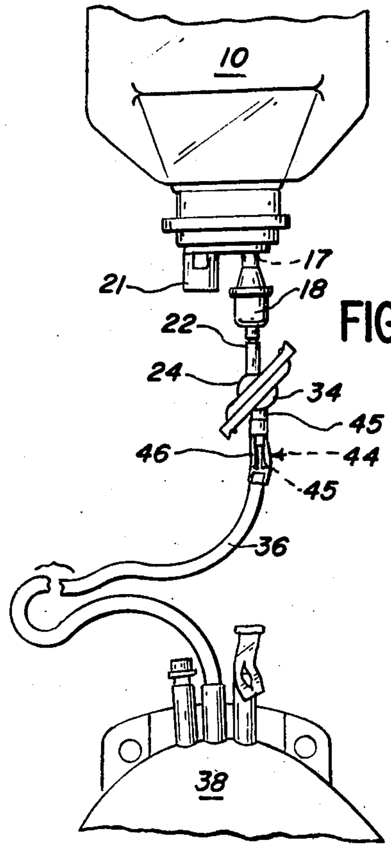
FIG. 3
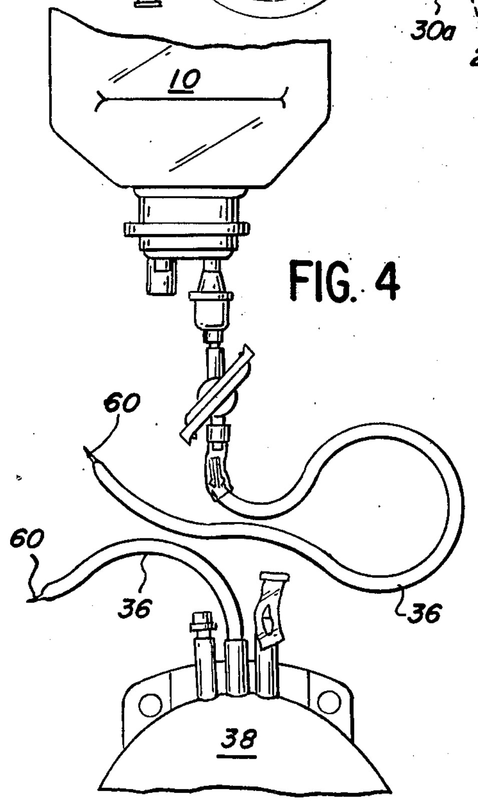
FIG. 4

ASEPTIC SYSTEM FOR TOTAL PARENTERAL NUTRITION AND THE LIKE

BACKGROUND ART

In parenteral solution administration it is of course necessary to maintain the highest aseptic standards.

Particularly in the area of total parenteral nutrition, where a patient is completely maintained for significant periods of time by nutrients administered parenterally, there is a significant need for preserving sterility when the various nutrient solutions are mixed for administration. Specifically, when dextrose or other carbohydrate solutions are mixed with amino acid or protein hydrolysate solutions, bacteria growth can be explosively rapid in the resulting mixture. Accordingly, extra care must be taken in such circumstances. Particularly, in the present techniques of use, such solutions are mixed only immediately before use despite their sterile environment, to avoid the risk of the explosive growth of bacteria.

However, it would be desirable to have a system which permits the safe mixing of parenteral solutions such as dextrose or other carbohydrate solutions with an amino acid or protein hydrolysate solution, while permitting the resulting mixture to be stored for a period of days. The hospital administration of such materials would be greatly facilitated by permitting the premixing of the materials.

In the present system, a standard Viaflex® container, which is a flat, collapsible bag manufactured by Travenol Laboratories, Inc., is initially about half-filled with a parenteral solution such as 50% Dextrose. Protein hydrolysate solution may be administered into the Viaflex bag through the end spike of an administration set which passes through a diaphragm port of the Viaflex bag, which diaphragm port is carried by the peripheral heat seal of the bag.

After the protein hydrolysate is passed through the set into the bag, filling it, the flexible tubing of the set may be conventionally sealed and then cut through the seal to separate the bag, so that the spike penetrating into the port of the Viaflex bag and a sealed section of tubing connected to the spike serves as a seal.

As stated above, such a system is not recommended for storage, but should be infused shortly after mixing.

By this invention, a system is provided in which large volume parenteral solutions and the like may be mixed without a reduction in their shelf life, so that protein hydrolysate and carbohydrates, for example, may be mixed for total parenteral nutrition and then stored for a period of days, awaiting the time of use.

Furthermore, a flexible, collapsible container of this invention is disclosed in which a flexible, tubular boot member of improved design is provided to avoid substantially outward expansion of the boot member as it is collapsed to advance a cannula through a diaphragm, for opening of the container. Thus, the boot member can operate in a crowded area adjacent other ports, since it does not expand into interfering contact with closely adjacent ports.

DISCLOSURE OF THE INVENTION

In accordance with this invention, a flexible, collapsible container for holding sterile solutions and for transferring and receiving solutions in a sterile manner is provided. The container comprises a closure carried on the container, a tubular port passing therethrough, and a connector member carried on the tubular port for providing sealed connection between the connector member and a corresponding connector member.

The connector member comprises housing means defining a transparent wall portion and a thermoplastic, opaque wall portion positioned as part of the wall of the housing means. Means are provided for connecting the housing means to a housing means of the corresponding connector member having a corresponding thermoplastic wall portion in such a manner as to bring the respective wall portions together into facing contact. As the result of this, upon exposure of the connected housings to radiant energy, the wall portions in facing contact can fuse together and open an aperture through contacting wall portions, to provide a connection between the interiors of the respective housings.

The tubular port defines a diaphragm sealing flow through the bore of the tubular port with the connector member being carried by a tubular cannula defining an inwardly-pointed spike adapted to penetrate the puncturable diaphragm means and a flexible, tubular boot member sealed to the tubular port and also sealingly carrying the cannula therein.

In accordance with this invention, the flexible, tubular boot member defines an outer end portion including a terminal portion sealed to the cannula. An annular, radial portion extends outwardly in substantially normal relation to the axis of the cannula, curving to join a generally cylindrical portion which, in turn, joins the remainder of the flexible tubular boot member. As the result of this, upon advancement of the cannula to rupture the diaphragm, the annular, radial portion deflects inwardly without forcing the generally cylindrical portion to expand substantially outwardly. As stated above, the containers of this application may be equipped with one or more additional ports in close proximity to at least part of the boot member. Thus, since the boot member does not have to expand outwardly for operation, the close proximity of other ports does not interfere with its action.

Furthermore, the above container is adapted to be placed in sealed flow-communicating relation with the corresponding connector member of an additional flexible, collapsible container. The corresponding connector member may be attached to at least one foot of flexible tubing with the flexible tubing communicating at its other end to the additional container. Thus the two containers, after connection to form an integral unit, may be placed at different vertical heights to facilitate the flow of solution from the one container to the other.

The corresponding connector member may be carried on a second cannula member associated with frangible means for initially closing flow through the flexible length of tubing, but capable of being opened from the exterior of the tubing in sterile manner. The frangible means may include a closed end wall positioned at the end of the cannula opposed to the connector member, with means being provided for rupturing the closed end wall to open the end upon manual manipulation thereof from the exterior of the tubing.

The tubular boot member may also define an annular ridge projecting outwardly and positioned circumferentially about a central portion thereof. This ridge provides hoop strength to the structure, and also serves as a molding aid in that it facilitates the gating of the molded tubular boot member, which is preferably made of an elastic latex material, for example natural rubber latex.

The circumferential ridge may be positioned at the inner end of the generally cylindrical portion of the member, opposed to the connector member which is carried thereby. The boot member may also define a portion which tapers inwardly from the annular ridge as it extends away from the annular ridge and connector member, the inwardly tapered portion being terminated with a cylindrical portion which, in turn, is sealed to the tubular port.

BRIEF DESCRIPTION OF DRAWINGS

Referring to the drawings,

FIG. 1 is an elevational view of the container of this invention, adapted to carry a parenteral solution such as a protein hydrolysate or amino acid solution, for example, associated with an additional flexible, collapsible container having an extension of flexible tubing and a connector member on the end thereof.

FIG. 2 is an enlarged fragmentary elevational view, with portions broken away, of the connector member and boot of the container of this invention.

FIG. 3 is a fragmentary elevational view showing the tube connectors placed into sterile, communicating relation for transfer of the contents of one of the containers to the other.

FIG. 4 is a fragmentary elevational view showing how the two containers may be separated after transfer of the contents.

BEST MODE FOR CARRYING OUT THE INVENTION

Referring to the drawings, flexible, collapsible container 10 is shown, being of any conventional design except as otherwise described herein, but specifically shown to be of a design as disclosed in U.S. Patent Application Ser. No. 126,228, filed Mar. 3, 1980 now U.S. Pat. No. 4,308,904. The container, which is wedge-shaped in its original form, collapses flat except for shoulder 12 to expel essentially all the contents of the container. Container 10 is shown to be about half-filled with a protein hydrolysate or amino acid solution.

Sealed to head 14 of container 10 is access port 16, with flexible, tubular boot member 18 being sealed at one end thereof to port 16, and sealed at its other end to rigid cannula 20, having a free, pointed inner end 22 penetrating into the interior of tubular boot member 18. Cannula spike 20 carries connector member 24, which may be of a known design.

Port 19 and other ports as may be desired are also present at the closed outer end of neck portion 14, with a pop-off cap 21 being provided to seal port 19, which may be used for the addition of supplemental medication, or may be a site to which an additional set may be connected, or the like. Because of the close proximity of port 19 and pop-off cap 21 to boot 18, it is desirable for the boot to collapse, as cannula spike 20 is advanced toward diaphragm 17 to penetrate it, in a manner in which boot 18 does not expand outwardly.

The inventive principle of the sterile connector 24 which is utilized in this invention is as described in Granzow et al. U.S. Pat. No. 4,157,723, as well as Ammann et al. Patent Application Ser. No. 005,749, filed Jan. 23, 1979 now U.S. Pat. No 4,265,280; Boggs et al. Patent Application Ser. No. 027,575, filed Apr. 6, 1979; now U.S. Pat. No. 4,325,417 and Bellamy et al. Patent Application Ser. No. 091,688, filed Nov. 5, 1979. The sterile connectors used for connector 24 may make use of any of the design features disclosed in the above-cited patent and pending applications.

As described above, connector 24 has housing means defining a transparent wall portion 26 and a thermoplastic, opaque wall portion 28 positioned as part of the wall of the housing means. In this specific embodiment, tongue 30 and groove 32 are provided to lockingly mate with a corresponding tongue 30*a* and groove 32*a* of a corresponding connector member 34 which may be of identical design to connector member 24, and is adapted to lock the opaque wall portions 28, 28*a* together into facing contact.

Then, the joined connector members 24, 34 are exposed to radiant energy as taught in the prior cited patent and applications, causing the wall portions in facing contact to fuse together to open an aperture through contacting wall portions, and at the same time to kill bacteria on the nonsterile surfaces of the wall portions by the high melting temperature of the wall portions 28, 28*a*. Accordingly, a sterile connection may be made between the two containers having nonsterile outer surfaces.

Alternatively, only one of wall portions 28, 28*a* has to be opaque, with the other wall portion being heated by conduction.

Connector 34 is carried on the end of flexible tubing 36 which may preferably be from about one to three feet in length, communicating with the interior of collapsible bag 38, which may be of a pair of peripherally heat-sealed polyvinyl chloride plastic sheets or the like, in accordance with a conventional design, for example a design similar to the Viaflex® containers sold by Travenol Laboratories, Inc. Container 38 may be approximately half-filled with a carbohydrate parenteral solution.

Bag 38 may also contain a conventional medicament addition port 40. Port 42 also may be present, and may serve as a connection port for solution administration.

Accordingly, connectors 24, 34 of the separate containers 10, 38 may be locked together in the manner illustrated in FIG. 3, with the opaque, thermoplastic wall portions 28, 28*a* being positioned in abutting, facing relationship. The joined connectors 26, 34 are then irradiated with infrared or light radiation in the known manner, causing the selective absorption of heat of the opaque portions 28, 28*a* compared with the transparent housing portion, with the result that opaque membranes 28, 28*a* fuse together and melt, opening a hole between them. When a preferably crystalline, high-melting thermoplastic is used for wall portions 28, 28*a* such as a carbon-filled poly(4-methyl-1-pentene), which is sold under the name TPX by Mitsui Chemical Company, the very melting step can result in a sterilizing bacteria kill since the melting and hole opening takes place at a temperature of 200° C. or above. Thus a sterile path is opened between connectors 24, 34.

Following the sterile connection between connectors 24, 34, as illustrated in FIG. 3, rupture of auxiliary seals behind each connector 24, 34 is effected. Tubing 36 of container 38 contains an internal auxiliary seal 44, carried on stiff cannula 45 attached to connector 34, which may, for example, be of the design disclosed in U.S. Pat. No. 4,181,140 or in U.S. Patent Application Ser. No. 086,102 filed Oct. 18, 1979 now U.S. Pat. No. 4,340,049. These internal seals include a closed wall of a cannula attached to sterile connector 34 with an elongated member projecting outwardly from the closed wall, with the structure being situated inside of a generally enlarged flexible tubing 46. Accordingly, projecting member 45 may be manually bent to rip away closed wall and to open flow through tubing 36.

The auxiliary seal for sterile connector 24 constitutes pointed cannula 20 having pointed end 22, which may be moved to pass through diaphragm 17 for sterile opening, collapsing boot 18 as it moves.

In accordance with this invention, boot member 18 defines an outer end portion including a terminal tubular portion 46 which is sealed to cannula 20.

An annular, radial portion 48 of boot member 18 extends radially outwardly in substantially normal relation to the axis of said cannula, curving through annular portion 50 to join a generally cylindrical portion 52 which, in turn, joins the remainder of the flexible boot member 18.

Annular ridge 54 projects outwardly from the member and is positioned circumferentially about a central portion thereof. Ridge 54 provides hoop strength to the boot member, and also its presence facilitates the molding of the hollow, tubular boot member 18, which may be made of a natural latex, for example.

As seen, circumferential ridge 54 is positioned at the inner end of generally cylindrical portion 52, opposed to connector member 24. Boot member also defines a portion 56 which tapers inwardly from annular ridge 54 as it extends away from the annular ridge 54 and connector member 24. The inwardly tapering portion 56 is then terminated with a cylindrical portion 58 which is sealed to tubular port 16.

As cannula 20 is advanced to puncture diaphragm 17, annular radial portion 48 is collapsed within boot member 18 as cannula 20 is advanced. However, due to the particular design of the boot member 18 of this invention, the walls of generally cylindrical portion 52 and tapered portion 56 do not expand outwardly to a significant extent, so that the collapsing boot member is not interfered with by the presence of adjacent ports and their closures, for example port 19 and pop-off cap 21.

Thus, the opening of both auxiliary ports to the sterile connectors 24, 34 can take place with ease. One purpose of the auxiliary ports is to prevent the contents of the containers from coming into contact with the interior of each sterile connector 24, 34 until after the connectors have been placed together and irradiated, to open the sterile connection between them. This avoids unexpected effects which may take place due to the presence of liquid container contents in the sterile connectors during the irradiation process.

After the opening steps, the contents of container 10, for example, may flow through the newly-opened, connected conduit to container 38 in a sterile manner, for example to mix protein hydrolysate with glucose solution in a manner permitting the continued storage of the mixture.

Following this, tubing 36 may be sealed to a flat, heat-sealed portion 60 by a conventional heat sealing device and severed through the middle of the heat seal. The remaining portion of tubing 36 which remains connected to container 10, and the container 10, may be discarded, while container 38 remains in sterile condition for further storage or use as may be desired.

The above has been offered for illustrative purposes only, and is not intended to limit the scope of this invention, which is as defined in the claims below.

That which is claimed is:

1. A flexible, collapsible container for holding sterile solution and for transferring and receiving solutions in a sterile manner, which comprises a closure carried on said container, a tubular port passing therethrough, and a connector member carried on said tubular port for providing sealed connection between said connector member and a corresponding connector member, said connector member comprising housing means defining a transparent wall portion and a thermoplastic, opaque wall portion positioned as part of the wall of said housing means, and means for connecting said housing means to a housing means of the corresponding connector member having a corresponding thermoplastic wall portion in such a manner as to bring the respective wall portions together into facing contact whereby, upon exposure of the connected housings to radiant energy, the wall portions in facing contact can fuse together and open an aperture through said contacting wall portions, to provide a connection between the interiors of the respective housings, said tubular port defining a diaphragm sealing flow through the bore of said tubular port, said connector member being carried by a tubular cannula defining an inwardly-pointed spike adapted to penetrate said puncturable diaphragm means and a flexible, tubular boot member sealed to said tubular port and also sealingly carrying said cannula therein, the improvement comprising, in combination:

the flexible, tubular boot member defining an outer end portion including a terminal portion sealed to said cannula, an annular radial portion extending radially outwardly in substantially normal relation to the axis of said cannula, and curving to join a generally cylindrical portion, which joins the remainder of the flexible, tubular boot member, said tubular boot member further including an annular ridge projecting outwardly and positioned circumferentially about a central portion of said boot member for substantially preventing the outward expansion of said generally cylindrical portion upon inward deflection of said annular radial portion.

2. The flexible, collapsible container of claim 1 in which the connector member is in sealed flow communicating relation with a corresponding connector member, said corresponding connector member being attached to at least 1 foot of flexible tubing, said flexible tubing communicating at its other end with an additional flexible, collapsible container.

3. The flexible, collapsible container of claim 2 in which said corresponding connector member is carried on a second cannula member associated with frangible means for initially closing flow through said flexible length of tubing, but capable of being opened from the exterior of said tubing in sterile manner.

4. The flexible, collapsible container of claim 3 in which said frangible means comprises a closed end wall positioned at the end of said cannula opposed to the connector member, and means for rupturing said closed end wall to open said end upon manual manipulation thereof from the exterior.

5. The flexible, collapsible container of claim 1 in which said annular ridge is positioned at the inner end of said generally cylindrical portion opposed to the connector member, and said boot member defines a portion which tapers inwardly from said annular ridge as it extends away from said annular ridge and connector member, said inwardly tapered portion being terminated with a cylindrical portion which is sealed to said tubular port.

6. The flexible, collapsible container of claim 5 in which said flexible tubular boot member is an integral piece of latex.

7. A flexible, collapsible container for holding sterile solution and for transferring and receiving solutions in a sterile manner, which comprises a closure carried on said container, a tubular port passing therethrough, and a connnector member carried on said tubular port for providing sealed connection between said connector member and a corresponding connector member, said tubular port defining a diaphragm sealing flow through the bore of said tubular port, said connector member being carried by a tubular cannula defining an inwardly pointed spike adapted to penetrate said puncturable diaphragm means and a flexible, tubular boot member sealed to said tubular port and also sealingly carrying said cannula therein, the improvement comprising, in combination:

the flexible, tubular boot member defining an outer end portion including a terminal portion sealed to said cannula, an annular radial portion extending radially outwardly in substantially normal relation to the axis of said cannula, and curving to join a generally cylindrical portion, which joins the remainder of the flexible, tubular boot member, said tubular boot member further including an annular ridge projecting outwardly and positioned circumferentially about a central portion of said boot member for substantially preventing the outward expansion of said generally cylindrical portion upon inward deflection of said annular radial portion.

8. The flexible, collapsible container of claim 7 in which the connector member is in sealed, flow communicating relation with a corresponding connector member, said corresponding connector member being attached to at least one foot of flexible tubing, said flexible tubing communicating at its outer end with an additional flexible, collapsible container.

9. The flexible, collapsible container of claim 7 in which said annular ridge is positioned at the inner end of said generally cylindrical portion opposed to the connector member, and said boot member defines a portion which tapers inwardly from said annular ridge as it extends away from said annular ridge and connector member, said inwardly tapered portion being terminated with a cylindrical portion which is sealed to said tubular port.

10. The flexible, collapsible container of claim 9 in which said flexible, tubular boot member is an integral piece of latex.

11. A flexible, collapsible container for holding sterile solution and for transferring and receiving solutions in a sterile manner, which comprises a closure carried on said container, a tubular port passing therethrough, and a connector member carried on said tubular port for providing sealed connection between said connector member and a corresponding connector member, said tubular port defining a diaphragm sealing flow through the bore of said tubular port, said connector member being carried by a tubular cannula defining an inwardly pointed spike adapted to penetrate said puncturable diaphragm means and a flexible, tubular boot member sealed to said tubular port and also sealingly carrying said cannula therein, the improvement comprising, in combination:

the flexible, tubular boot member defining an outer end portion including a terminal portion sealed to said cannula, an annular radial portion extending radially outwardly in substantially normal relation to the axis of said cannula, and curving to join a generally cylindrical portion, which joins the remainder of the flexible, tubular boot member, said tubular boot member further including an annular ridge projecting outwardly and positioned circumferentially both at the inner end of said generally cylindrical portion opposed to the connector member and about the central portion of said tubular boot member, said tubular boot member defining a portion which tapers inwardly from said annular ridge as it extends away from said annular ridge and connector member, said inwardly tapered portion terminating with a cylindrical portion sealed to said tubular port.

* * * * *

UNITED STATES PATENT AND TRADEMARK OFFICE
CERTIFICATE OF CORRECTION

PATENT NO. : 4,368,729

DATED : January 18, 1983

INVENTOR(S) : Luc M. Dossin

It is certified that error appears in the above-identified patent and that said Letters Patent are hereby corrected as shown below:

In Claim 8, line 40, change the word "outer" to read -- other --.

Signed and Sealed this

*Twelfth* Day of *April 1983*

[SEAL]

*Attest:*

GERALD J. MOSSINGHOFF

*Attesting Officer* *Commissioner of Patents and Trademarks*